US008990025B2

(12) United States Patent
Potyrailo et al.

(10) Patent No.: US 8,990,025 B2
(45) Date of Patent: Mar. 24, 2015

(54) TEMPERATURE-INDEPENDENT CHEMICAL AND BIOLOGICAL SENSORS

(71) Applicant: General Electric Company, Schenectady, NY (US)

(72) Inventors: Radislav Alexandrovich Potyrailo, Niskayuna, NY (US); Cheryl Margaret Surman, Albany, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/031,965

(22) Filed: Sep. 19, 2013

(65) Prior Publication Data

US 2014/0019067 A1    Jan. 16, 2014

Related U.S. Application Data

(62) Division of application No. 12/977,599, filed on Dec. 23, 2010, now Pat. No. 8,542,024.

(51) Int. Cl.
*G01N 27/02* (2006.01)
*G01N 33/487* (2006.01)

(52) U.S. Cl.
CPC .............. *G01N 27/02* (2013.01); *G01N 27/025* (2013.01); *G01N 33/48792* (2013.01)
USPC ............... 702/25; 324/633; 702/19; 702/22

(58) Field of Classification Search
CPC .. G01N 27/02; G01N 27/122; G01N 33/0004; G01N 27/3278; G01N 33/48792; G01N 2291/0256; G01N 27/021; G01N 29/036; G01G 3/16; G06K 19/0717; G06K 19/07749
USPC .......... 702/19, 23, 25, 22; 324/602, 633, 652, 324/655; 73/31.05, 64.53; 310/360; 340/10.41
See application file for complete search history.

(56) References Cited

U.S. PATENT DOCUMENTS 5,744,902 A    4/1998    Vig
8,547,110 B2 *  10/2013    Kesil et al. .................... 324/633
(Continued)

FOREIGN PATENT DOCUMENTS

WO    2007139574 A1    12/2007
WO    2011053234 A1    5/2011
WO    2012002877 A1    1/2012

OTHER PUBLICATIONS

Potyrailo, R., et al.; Development of Radio-Frequency Identification Sensors Based on Organic Electronic Sensing Materials for Selective Detection of Toxic Vapors; American Institute of Physics, Journal of Applied Physics 106, 124902 (2009), pp. 124902-1 through 124902-6 (6 pages).
Potyrailo, R., et al.; Selective Quantitation of Vapors and their Mixtures using Individual Passive Multivariable RFID Sensors; IEEE RFD; 2010; pp. 22-28 (7 pages).
Potyrailo, R., et al.; RFID Sensors based on Ubiquitous Passive 13.56-MHz RFID Tags and Complex Impedance Detection; 2008 John Wiley & Sons, Ltd. (13 pages).
(Continued)

*Primary Examiner* — John H Le
(74) *Attorney, Agent, or Firm* — Jean K. Testa; Fletcher Yoder, P.C.

(57) ABSTRACT

Methods and sensors for selective fluid sensing are provided. A sensor includes a resonant inductor-capacitor-resistor (LCR) circuit and a sensing material disposed over a sensing region. The sensing region comprises at least a portion of the LCR circuit. Temperature-dependent response coefficients of inductance L, capacitance C, and resistance R properties of the LCR circuit and the sensing material are at least approximately 5 percent different from one another. The difference in the temperature-dependent response coefficients of the properties of the LCR circuit and the sensing material enables the sensor to selectively detect analyte fluids from an analyzed fluid mixture substantially independent of temperature.

20 Claims, 7 Drawing Sheets

(56) References Cited

U.S. PATENT DOCUMENTS

| | | |
|---|---|---|
| 2007/0090926 A1 | 4/2007 | Potyrailo et al. |
| 2008/0177150 A1 | 7/2008 | Ii et al. |
| 2009/0278685 A1 | 11/2009 | Potyrailo et al. |
| 2012/0116683 A1* | 5/2012 | Potyrailo et al. ............... 702/19 |
| 2014/0025313 A1* | 1/2014 | Potyrailo et al. ............... 702/23 |

OTHER PUBLICATIONS

Tan, E., et al.; A Wireless, Passive Sensor for Quantifying Packaged Food Quality; Sensors ISSN 1424-8220; Sep. 5, 2007; 7, 1747-1756 (10 pages).

GB Search Report dated Mar. 28, 2012 from corresponding Application No. GB1121548.0.

* cited by examiner

TEMPERATURE-INDEPENDENT CHEMICAL AND BIOLOGICAL SENSORS

CROSS REFERENCE TO RELATED APPLICATIONS

This application is a divisional of U.S. patent application Ser. No. 12/977,599, entitled "Temperature-Independent Chemical and Biological Sensors", filed Dec. 23, 2010, which is herein incorporated by reference.

STATEMENT REGARDING FEDERALLY SPONSORED RESEARCH & DEVELOPMENT

This invention was made with Government support and funded in part by the National Institute of Environmental Health Sciences under Grant No. 1R01ES016569-01A1. The Government has certain rights in the invention.

BACKGROUND

The subject matter disclosed herein relates to chemical and biological sensors, and more particularly, to highly selective temperature-independent chemical and biological sensors.

Chemical and biological sensors are often employed in a number of applications where the detection of various vapors may be used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications, such as residential home monitoring, home land security in airports, in different environmental and clinical settings, and other public venues wherein detection of certain harmful and/or toxic vapors may be particularly useful.

One technique for sensing such environmental changes is by employing a sensor, such as an RFID sensor, coated with a particular sensing material. In addition, sensors may be arranged in an array of individual transducers, which are coated with one or more sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In certain applications multiple responses or changes in multiple properties may occur. In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response, complicates fabrication of the array.

Further, in many practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, high humidity environments often interfere with the ability of traditional sensors to detect selected vapors. Furthermore, temperature variations reduce the accuracy of chemical and biological sensing when sensors are employed as individual sensors or arranged in an array.

Various embodiments disclosed herein may address one or more of the challenges set forth above.

BRIEF DESCRIPTION

In accordance with one embodiment, there is provided a sensor comprising a resonant inductor-capacitor-resistor (LCR) circuit and a sensing material disposed over a sensing region. The sensing region comprises at least a portion of the LCR circuit. Temperature-dependent response coefficients of inductance L, capacitance C, and resistance R properties of the LCR circuit and the sensing material are at least approximately 5 percent different from one another. The difference in the temperature-dependent response coefficients of the properties of the LCR circuit and the sensing material enables the sensor to selectively detect analyte fluids from an analyzed fluid mixture substantially independent of temperature.

In accordance with another embodiment, there is provided a method of detecting chemical or biological species in a fluid. The method comprises measuring a real part and an imaginary part of an impedance spectrum of a resonant sensor antenna coated with a sensing material. The temperature-dependent response coefficients of a property of the resonant sensor antenna and the sensing material are different from one another. The method further comprises calculating at least six spectral parameters of the resonant sensor antenna coated with the sensing material at a plurality of temperatures. The method further comprises reducing the impedance spectrum to a single data point using multivariate analysis to selectively identify an analyte. The method further comprises determining one or more environmental parameters from the impedance spectrum using stored calibration coefficients. The determination of the one or more environmental parameters is substantially independent of temperature.

In accordance with another embodiment, there is provided a method of manufacturing a sensor. The method includes assembling a transducer comprising a resonant inductor-capacitor-resistor (LCR) circuit. The transducer comprises at least three temperature-dependent response coefficients of inductance L, capacitance C, and resistance R properties of the LCR circuit. The at least three temperature-dependent response coefficients of the properties of the LCR circuit are at least approximately 5 percent different from one another. The method further includes selecting a sensing material that comprises at least two temperature-dependent response coefficients of dielectric constant and resistance properties of the sensing material. The at least two temperature-dependent response coefficients of the properties of the sensing material are at least approximately 5 percent different from the at least three temperature-dependent response coefficients of the properties of the LCR circuit. The method further includes disposing the sensing material over a sensing region. The sensing region comprises at least a portion of the LCR circuit.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments disclosed herein provide temperature-independent methods and systems for selective vapor sensing wherein a single sensor is provided and is capable of detecting multiple vapors and/or mixtures of vapors alone, or in the presence of one another. Examples of general methods for vapor sensing using a single sensor are described in U.S. patent application Ser. No. 12/942,732 entitled "Highly Selective Chemical and Biological Sensors," which is incorporated herein by reference. The disclosed sensors are capable of detecting different vapors and mixtures in the presence of variable temperature even in a high humidity environment or an environment wherein one or more vapors has a substantially higher concentration (e.g. 10×) compared to other components in the mixture. Each sensor includes a resonant inductor-capacitor-resistor (LCR) sensor that is coated with a sensing material. Temperature-dependent response coefficients of a property of the LCR circuit and the sensing material are different from one another. The differences in the temperature-dependent response coefficients of the property affect the measurements of the disclosed sensors. However, knowledge of the temperature-dependent response coefficients of the property and/or knowledge of how the sensor is affected by the differences in the temperature-dependent response coefficients of the property are used together with multivariate analysis of the measured impedance of the sensor to provide temperature-independent selective vapor sensing and improved stability of response. For example, a look-up table may be developed that includes coefficients based on experimental testing of the sensor. During use of the sensor, the experimentally determined coefficients may be used in the multivariate analysis to account for variations in temperature during sensing. Other embodiments disclosed herein provide temperature-independent methods and systems for selective chemical and biological sensing wherein a single sensor is provided and is capable of detecting multiple chemical or biological species in liquids and/or mixtures of chemical or biological species alone, or in the presence of one another.

Non-limiting examples of LCR sensors include RFID sensors with an integrated circuit (IC) memory chip, RFID sensors with an IC chip, and RFID sensors without an IC memory chip (chipless RFID sensors). LCR sensors can be wireless or wired. In order to collect data, an impedance spectrum is acquired over a relatively narrow frequency range, such as the resonant frequency range of the LCR circuit. The technique further includes calculating the multivariate signature from the acquired spectrum and manipulating the data to discern the presence of certain vapors and/or vapor mixtures. The presence of vapors is detected by measuring the changes in dielectric, dimensional, charge transfer, and other changes in the properties of the materials employed by observing the changes in the resonant electronic properties of the circuit. By using a mathematical procedure, such as principal component analysis (PCA) and others, multiple vapors and mixtures can be detected in the presence of one another and in the presence of an interferent as further described below. Embodiments disclosed herein provide temperature-independent methods and systems for selective fluid sensing wherein a single sensor is provided and is capable of detecting multiple fluids and/or mixtures of fluids alone, or in the presence of one another. Further embodiments disclose methods for manufacturing such sensors by assembling a transducer that includes the LCR circuit and disposing the sensing material over at least a portion of the transducer, where the temperature-dependent response coefficients of a property of the transducer and the sensing material are different from one another. In other embodiments, besides chemical sensors for vapors and fluids, biological sensors may also have temperature-independent detection capabilities.

To more clearly and concisely describe the subject matter of the claimed invention, the following definitions are provided for specific terms, which are used in the following description and the appended claims.

The term "fluids" includes gases, vapors, liquids, particles, biological particles, biological molecules, and solids.

The term "digital ID" includes all data stored in a memory chip of the RFID sensor. Non-limiting examples of this data are manufacturer identification, electronic pedigree data, user data, and calibration data for the sensor.

The term "monitoring process" includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady state measurements of individual vapors and their mixtures.

The term "environmental parameters" is used to refer to measurable environmental variables within or surrounding a manufacturing or monitoring system. The measurable environmental variables comprise at least one of physical, chemical, and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

The term "analyte" includes any desired measured environmental parameter.

The term "interference" includes any undesired environmental parameter that undesirably affects the accuracy and precision of measurements with the sensor. The term "interferent" refers to a fluid or an environmental parameter (that includes, but is not limited to temperature, pressure, light, etc.) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. The term "principal components analysis (PCA)" refers to a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum (its both real and imaginary parts) may be analyzed simultaneously using various parameters for analysis, such as, the frequency of the maximum of the real part of the impedance ($F_p$), the magnitude of the real part of the impedance ($Z_p$), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors." The appropriate selection of features is performed from all potential features that can be calculated from spectra. Multivariable spectral parameters are described in U.S. patent application Ser. No. 12/118,950 entitled "Methods and systems for calibration of RFID sensors," which is incorporated herein by reference.

The term "resonance impedance" or "impedance" refers to measured sensor frequency response around the resonance of the sensor from which the sensor "spectral parameters" are extracted.

The term "protecting material" includes, but is not limited to, materials on the LCR or RFID sensor that protect the sensor from an unintended mechanical, physical or chemical effect while still permitting the anticipated measurements to be performed. For example, an anticipated measurement may include solution conductivity measurement wherein a protecting film separates the sensor from the liquid solution yet allows an electromagnetic field to penetrate into solution. An example of a protecting material is a paper film that is applied on top of the sensor to protect the sensor from mechanical damage and abrasion. Another non-limiting example of a protecting material is a polymer film that is applied on top of the sensor to protect the sensor from corrosion when placed in a liquid for measurements. A protecting material may also be a polymer film that is applied on top of the sensor for protection from shortening of the sensor's antenna circuit when placed in a conducting liquid for measurements. Non-limiting examples of protecting films are paper, polymeric, and inorganic films such as polyesters, polypropylene, polyethylene, polyethers, polycarbonate, polyethylene tereptphalate, zeolites, metal-organic frameworks, and cavitands. The protecting material can be arranged between the transducer and sensing film to protect the transducer. The protecting material can be arranged on top of the sensing film which is itself is on top of the transducer to protect the sensing film and transducer. The protecting material on top of the sensing film which is itself is on top of the transducer can serve to as a filter material to protect the sensing film from exposure to gaseous or ionic interferences. Non-limiting examples of filter materials include zeolites, metal-organic frameworks, and cavitands.

As used herein the term "sensing materials and sensing films" includes, but is not limited to, materials deposited onto a transducer's electronics module, such as LCR circuit components or an RFID tag, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the LCR or RFID sensor, the impedance sensor response changes as a function of pH. Thus, such an LCR or RFID sensor works as a pH sensor. When such a polyaniline film is deposited onto the LCR or RFID sensor for detection in gas phase, the impedance sensor response also changes upon exposure to basic (for example, $NH_3$) or acidic (for example, HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensing material. In order to prevent the material in the sensor film from leaching into the liquid environment, the sensing materials are attached to the sensor surface using standard techniques, such as covalent bonding, electrostatic bonding, and other standard techniques known to those of ordinary skill in the art. In addition, the sensing material has at least two temperature-dependent response coefficients related to temperature-dependent changes in material dielectric constant and resistance of the sensing material.

The terms "transducer and sensor" are used to refer to electronic devices such as RFID devices intended for sensing. "Transducer" is a device before it is coated with a sensing or protecting film or before it is calibrated for a sensing application. The transducer includes at least three temperature-dependent response coefficients of temperature-dependent changes in capacitance C, resistance R, and inductance L of the LCR circuit. "Sensor" is a device typically after it is coated with a sensing or protecting film and after being calibrated for the sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information and modulating and demodulating a radio frequency signal. This memory chip can also be used for other specialized functions, for example, it can contain a capacitor. It can also contain at least one input for an analog signal such as resistance input, capacitance input, or inductance input. In the case of a chipless RFID tag, the RFID tag may not include an IC memory chip. This type of RFID tag may be useful in applications where a specific RFID tag does not need to be identified, but rather a signal merely indicating the presence of the tag provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters." The "RFID sensor" can have an integrated circuit (IC) memory chip attached to the antenna or can have no IC memory chip. An RFID sensor without an IC memory chip is an LCR sensor. An LCR sensor is comprised of known components, such as at least one inductor (L), at least one capacitor (C), and at least one resistor (R) to form an LCR circuit.

The term "single-use container" includes, but is not limited to, manufacturing or monitoring equipment, and packaging, which may be disposed of after use or reconditioned for reuse. Single-use packaging in the food industry includes, but is not limited to, food and drinks packaging, and candy and confection boxes. Single-use monitoring components include, but are not limited to, single-use cartridges, dosimeters, and collectors. Single use manufacturing containers include, but are not limited to, single-use vessels, bags, chambers, tubing, connectors, and columns.

The term "writer/reader" includes, but is not limited to, a combination of devices to write and read data into the memory of the memory chip and to read impedance of the antenna. Another term for "writer/reader" is "interrogator."

In accordance with embodiments disclosed herein, an LCR or an RFID sensor for sensing vapors, vapor mixtures, chemical, and biological species is described. As previously described, the RFID sensor includes an RFID tag coated with a sensing material with temperature-dependent response coefficients of a property different from that of the LCR circuit. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through the antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements. The distance between the "RFID sensor" without an IC memory chip (chipless RFID sensor or LCR sensor or LCR transducer) and the sensor reader is governed by the design parameters that include operating frequency, RF or microwave power level, the receiving sensitivity of the sensor reader, and antenna dimensions.

In one embodiment a passive RFID tag with or without an IC memory chip may be employed. Advantageously, a passive RFID tag does not rely on a battery for operation. However, the communication distance between the writer/reader and RFID tag is typically limited within a proximity distance because the passive tag operates with only microwatts of RF power from the writer/reader. For passive tags operating at 13.56 MHz, the read distance is typically not more than several centimeters. The typical frequency range of operation of 13.56 MHz passive RFID tags for digital ID writing/reading is from 13.553 to 13.567 MHz. The typical frequency range of operation of 13.56-MHz passive RFID sensors for sensing of environmental changes around the RFID sensor is from about 5 MHz to about 20 MHz, more preferably from 10 to 15 MHz. The requirement for this frequency range is to be able to recognize the tag with a writer/reader that operates at 13.56 MHz while the sensor portion of the RFID tag operates from 5 to 20 MHz.

Depositing sensing films onto passive RFID tags creates RFID chemical or biological sensors. RFID sensing is performed by measuring changes in the RFID sensor's impedance as a function of environmental changes around the sensor, as described further below. If the frequency response of the antenna coil, after deposition of the sensing film, does not exceed the frequency range of operation of the tag, the information stored in the microchip can be identified with a conventional RFID writer/reader. An impedance analyzer (sensor reader) can read the impedance of the antenna coil to correlate the changes in impedance to the chemical and biological species of interest and to correct for temperature instabilities around the sensor.

In operation, after coating of the RFID tag with a chemically sensitive film, both the digital tag ID and the impedance of the tag antenna may be measured. The measured digital ID provides information about the identity of the tag itself, such as an object onto which this tag is attached, and the properties of the sensor (e.g. calibration curves for different conditions, manufacturing parameters, expiration date, etc.). For multi-component detection, multiple properties from the measured real and imaginary portions of the impedance of a single RFID sensor may be determined, as described further below.

In summary, and in accordance with the embodiments described herein, in order to achieve detection of analytes in the presence of temperature variations, the sensor should exhibit a number of characteristics. First, the selected transducer should include a multivariate output to independently detect the effects of different environmental parameters on the sensor. Second, the sensing material should have a preserved magnitude of response to an analyte over a wide range of temperature changes. The response to the relatively small analyte concentrations should not be fully suppressed by the relatively large temperature changes. Third, the temperature-effected responses of the sensing material and transducer are allowed but should be in a different direction of the multivariate output response of the transducer.

To achieve these characteristics, in one embodiment, the sensing material has multiple response mechanisms to vapors where these response mechanisms are related to the changes of dielectric constant, resistance, and swelling of the sensing material where these changes are not fully correlated with each other and produce different patterns upon exposure to individual vapors and their mixtures. Further, the LCR transducer can have multiple components of LCR response from the LCR circuit where these multiple components of LCR response originate from the different factors affecting the transducer circuit with the non-limiting examples that include material resistance and capacitance, contact resistance and capacitance between the transducer and sensing material, and resistance and capacitance between the transducer substrate and sensing material. Further, the LCR transducer can have multiple conditions of LCR circuit operation where an integrated circuit chip is a part of the sensor circuit.

Thus, one method for controlling the temperature-corrected sensor response involves powering of the integrated circuit chip to affect the impedance spectral profile. The different impedance spectral profiles change the temperature-dependent sensor response based upon interactions with different vapors, and chemical and biological species. The IC chip or IC memory chip on the resonant antenna contains a rectifier diode and it can be powered at different power levels to influence the impedance spectral profile of the sensor. The differences in spectral profiles at different power levels are pronounced in different values of $F_p$, $F_1$, $F_2$, $F_z$, $Z_p$, $Z_1$, $Z_2$, and calculated values of C and R. In one embodiment, the enhanced temperature-independent sensor performance is achieved through the appropriate selection of at least one power level of the IC chip or IC memory chip operation. In another embodiment, the enhanced temperature-independent sensor performance is achieved through the appropriate selection of at least two power levels of the IC chip or IC memory chip operation and analyzing the combined impedance spectral profiles of the sensor under different power levels. Powering of the sensor with at least two power levels is performed in the alternating fashion between a relatively low and relatively high power. The alternating powering of the sensor with at least two power levels is performed on the time scale that is at least 5 times faster than the dynamic changes in the measured environmental parameters. In all these embodiments, powering at different power levels is in the range from −50 dBm to +40 dBm and provides the ability to achieve temperature-independent sensor performance.

The improved temperature-independent LCR circuit operation is provided by varying the operation power of the integrated circuit chip to enhance the temperature-dependent response. In particular, sensor calibration for temperature-independent operation is performed with at least two power levels of operation of the integrated circuit chip of the sensor. The sensor is first operated at an appreciably low power so the integrated circuit chip is substantially turned off (power is between approximately −50 dBm to −10 dBm) and the temperature-dependent coefficients of the transducer and the sensing material are determined in the presence and absence of the analytes. Next, the sensor is operated at an appreciably high power so the integrated circuit chip is substantially turned on (power is between approximately −10 dBm to +40 dBm) and the temperature-dependent coefficients of the transducer and the sensing material are determined in the presence and absence of the analytes.

Figure 1:
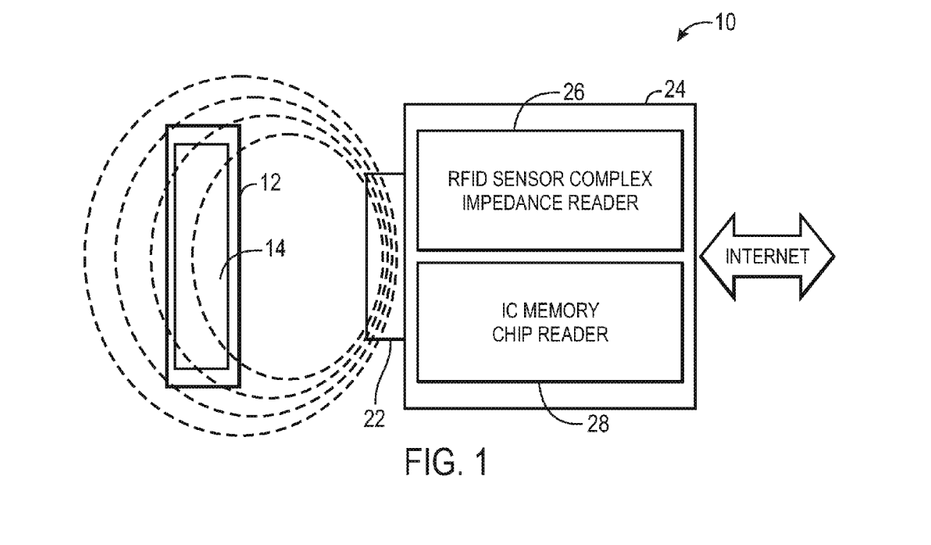
FIG. 1 illustrates a sensing system, in accordance with embodiments of the invention.
Figure 2:
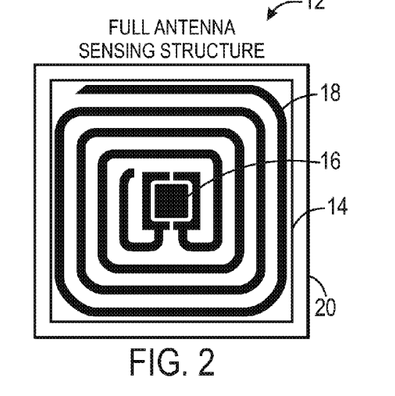
FIG. 2 illustrates an RFID sensor, in accordance with embodiments of the invention.

Turning now to the figures and referring initially to FIG. 1, a sensing system 10 is provided to illustrate the principle of temperature-independent selective vapor sensing utilizing an RFID sensor 12 having a sensing material 14 coated thereon. The sensing material 14 has at least two temperature-dependent response coefficients of dielectric constant and resistance properties. Referring briefly to FIG. 2, the sensor 12 is a resonant circuit that includes an inductor-capacitor-resistor structure (LCR) coated with the sensing material 14. The LCR structure comprises at least three temperature-dependent response coefficients of inductance L, capacitance C, and resistance R properties of the LCR circuit. The at least three temperature-dependent response coefficients of the properties of the LCR circuit are at least approximately 5 percent different from one another. In addition, the at least two temperature-dependent response coefficients of the properties of the sensing material 14 are at least approximately 5 percent different from the at least three temperature-dependent response coefficients of the properties of the LCR circuit. The sensing material 14 is applied onto the sensing region between the electrodes, which form sensor antenna 18 that constitute the resonant circuit. As will be described further below, by applying the sensing material 14 onto the resonant circuit, the impedance response of the circuit will be altered. The sensor 12 may be a wired sensor or a wireless sensor. The sensor 12 may also include a memory chip 16 coupled to resonant antenna 18 that is coupled to a substrate 20. The memory chip 16 may include manufacturing, user, calibration and/or other data stored thereon. The memory chip 16 is an integrated circuit device and it includes RF signal modulation circuitry fabricated using a complementary metal-oxide semiconductor (CMOS) process and a non-volatile memory. The RF signal modulation circuitry components include a diode rectifier, a power supply voltage control, a modulator, a demodulator, a clock generator, and other components.

Figure 3:
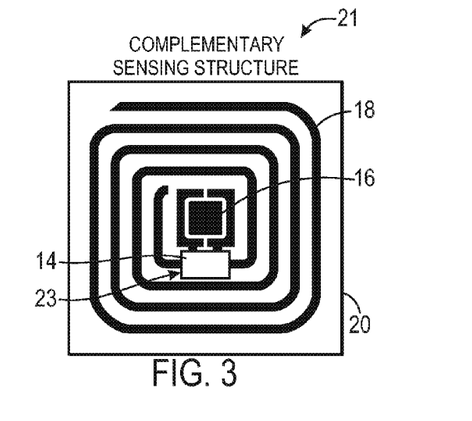
FIG. 3 illustrates an RFID sensor, in accordance with alternate embodiments of the invention.

FIG. 3 illustrates an alternative embodiment of the sensor 12, designated by reference numeral 21, wherein a complementary sensor 23 comprising the sensing material 14 is attached across the antenna 18 and the integrated circuit (IC) memory chip 16 to alter the sensor impedance response. In another embodiment (not illustrated), a complementary sensor may be attached across an antenna that does not have an IC memory chip and alters sensor impedance response. Non-limiting examples of complementary sensors are interdigitated sensors, resistive sensors, and capacitive sensors. Complementary sensors are described in U.S. patent application Ser. No. 12/118,950 entitled "Methods and systems for calibration of RFID sensors," which is incorporated herein by reference.

In one embodiment, a 13.56 MHz RFID tag may be employed. During operation of the sensing system 10, the impedance Z(f) of the sensor antenna 18 and the digital sensor calibration parameters stored on the memory chip 16 may be acquired. Referring again to FIG. 1, measurement of the resonance impedance Z(f) of the antenna 18 and the reading/writing of digital data from the memory chip 16 are performed via mutual inductance coupling between the RFID sensor antenna 18 and the pickup coil 22 of a reader 24. As illustrated, the reader 24 may include an RFID sensor impedance reader 26 and an integrated circuit memory chip reader 28. The interaction between the RFID sensor 12 and the pickup coil 22 can be described using a general mutual inductance coupling circuit model. The model includes an intrinsic impedance $Z_C$ of the pickup coil 22 and an intrinsic impedance $Z_S$ of the sensor 12. The mutual inductance coupling M and the intrinsic impedances $Z_C$ and $Z_S$ are related through the total measured impedance $Z_T$ across the terminal of the pickup coil 22, as represented by the following equation:

$$Z_T = Z_C + (\omega^2 M^2 / Z_S), \quad (1)$$

wherein ω is the radian carrier frequency and M is the mutual inductance coupling M coefficient.

Sensing is performed via monitoring of the changes in the properties of the sensing material 14 as probed by the electromagnetic field generated in the antenna 18 (FIG. 2). Upon reading the RFID sensor 12 with the pickup coil 22, the electromagnetic field generated in the sensor antenna 18 extends out from the plane of the sensor 12 and is affected by the dielectric property of an ambient environment providing the opportunity for measurements of physical, chemical, and biological parameters.

Sensing is performed via monitoring of the changes in the properties of the sensing material 14 as probed by the electromagnetic field generated in the complementary sensor 23 (FIG. 3). Upon reading the RFID sensor 12 with the pickup coil 22, the electromagnetic field generated in the complementary sensor 23 extends out from the plane of the complementary sensor 23 and is affected by the dielectric property of an ambient environment providing the opportunity for measurements of physical, chemical, and biological parameters.

Figure 4:
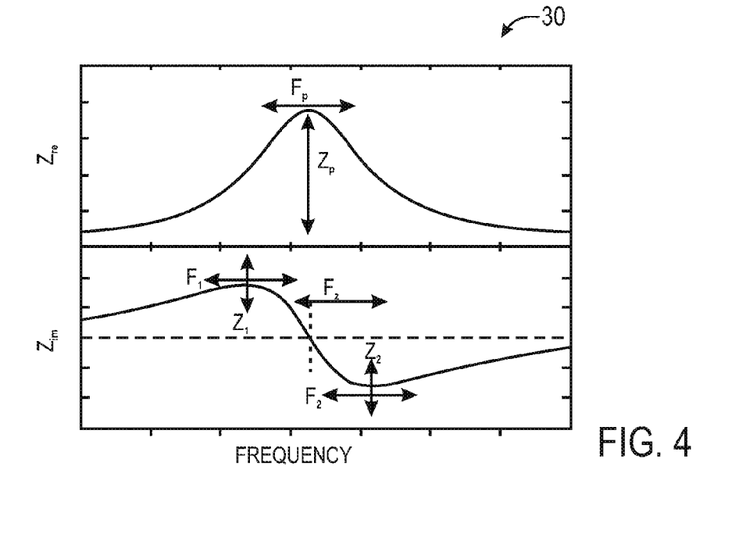
FIG. 4 illustrates measured responses of an RFID sensor, in accordance with embodiments of the invention.

FIG. 4 illustrates an example of measured responses of an exemplary RFID sensor 12, in accordance with embodiments of the invention, which includes the sensor's full impedance spectra and several individually measured spectral parameters. To selectively detect several vapors or fluids using a single RFID sensor, such as the RFID sensor 12, the real $Z_{re}(f)$ and imaginary $Z_{im}(f)$ parts of the impedance spectra $Z(f) = Z_{re}(f) + jZ_{im}(f)$ are measured from the sensor antenna 18 coated with a sensing material and at least four spectral parameters are calculated from the measured $Z_{re}(f)$ and $Z_{im}(f)$, as illustrated in the plot 30 of FIG. 4. Seven spectral parameters can be calculated as illustrated in the plot 30 of FIG. 4. These parameters include the frequency position $F_p$ and magnitude $Z_p$ of $Z_{re}(f)$, the resonant $F_1$ and anti-resonant $F_2$ frequencies of $Z_{im}(f)$, the impedance magnitudes $Z_1$ and $Z_2$ at $F_1$ and $F_2$ frequencies, respectively, and the zero-reactance frequency $F_Z$. Additional parameters, such as quality factor may also be calculated. From the measured parameters, resistance R, capacitance C, and other parameters of the sensing film-coated resonant antenna 18 can be also determined Multivariate analysis may be used to reduce the dimensionality of the impedance response, either from the measured real $Z_{re}(f)$ and imaginary $Z_{im}(f)$ parts of the impedance spectra or from the calculated parameters $F_p$, $Z_p$, $F_1$ and $F_2$, and possibly other parameters to a single data point in multidimensional space for selective quantization of different vapors or fluids, as will be appreciated by those skilled in the art, and as will be described further below.

The well-accepted limitations of impedance spectroscopy in practical sensors for trace analyte detection include relatively low sensitivity and prohibitively long acquisition times over the broad frequency range. Embodiments described herein enhance the ability to measure changes in properties of the sensing material by putting the material onto the electrodes of the resonant LCR sensor circuit. Similarly, the disclosed embodiments enhance the ability to measure changes in properties of the fluid in proximity to the electrodes of the resonant LCR sensor circuit. Experimental testing examined the effects of changing dielectric constant on sensing electrodes both with and without a resonator. Compared to the conventional impedance spectroscopy, the bare resonant LCR sensor provided an at least 100-fold enhancement in the signal-to-noise (SNR) over the smallest measured range of Δ∈ with the corresponding improvement of detection limit of dielectric constant determinations.

Performance of the LCR sensor as analyzed using multivariate analysis tools provides an advantage of improved selectivity over the processing of individual responses of individual sensors. In particular, test results indicate the relations between $F_p$ and $Z_p$ and the relations between calculated sensor resistance R and calculated sensor capacitance C have much less selectivity between responses to different vapors or fluids as compared to the relations between multivariable parameters that show more variation, as discussed in detail below. Further, the LCR sensors demonstrate independent contact resistance and contact capacitance responses that improve the overall selectivity of the multivariable response of the LCR sensors. This selectivity improvement originates from the independent contributions of the contact resistance and contact capacitance responses to the equivalent circuit response of the sensor.

The various components of the RFID sensor, such as sensors 12 and 21 illustrated in FIGS. 1-3, each possess various physical properties, such as, but not limited to, thermal conductivity, thermal expansion, elastic modulus, electrical resistance, impedance, and so forth. Such properties may be affected by changes in temperature. Thus, the temperature-dependent response coefficient of a property is defined as the relative change of the property when the temperature is changed by a fixed amount, such as 1 degree Celsius. The property may vary with temperature in a linear manner or polynomially, logarithmically, or exponentially, for example. Some properties may increase with temperature and other properties may decrease with temperature. For example, the temperature-dependent response coefficient of impedance may differ between the sensing material 14 and another component of the RFID sensor 12 or 21, such as, but not limited to, the memory chip 16, antenna 18, substrate 20, coil 22, integrated circuit (IC) chip, transducer, or film. In other words, the impedance of the sensing material 14 may vary with temperature differently than the other components of the RFID sensor 12 or 21. For example, for a change in temperature of 1 degree Celsius, the impedance of the sensing material 14 may increase by 1 ohm. In contrast, for the same change in temperature of 1 degree Celsius, the impedance of the antenna 18 of the RFID sensor 12 or 21 may increase by 0.8 ohm. Thus, the percent different between the two temperature-dependent response coefficients of impedance is approximately 22 percent. In various embodiments, the absolute values of temperature-dependent response coefficients of a property of the LCR circuit and the sensing material 14 may be between approximately 0.5 percent to 500 percent, 2 percent to 100 percent, or 5 percent to 50 percent. Based on the differences in the temperature-dependent response coefficients of the LCR circuit and the sensing material 14, the RFID sensor 12 or 21 may selectively detect analyte fluids from an analyzed fluid mixture substantially independent of temperature.

Figure 5:
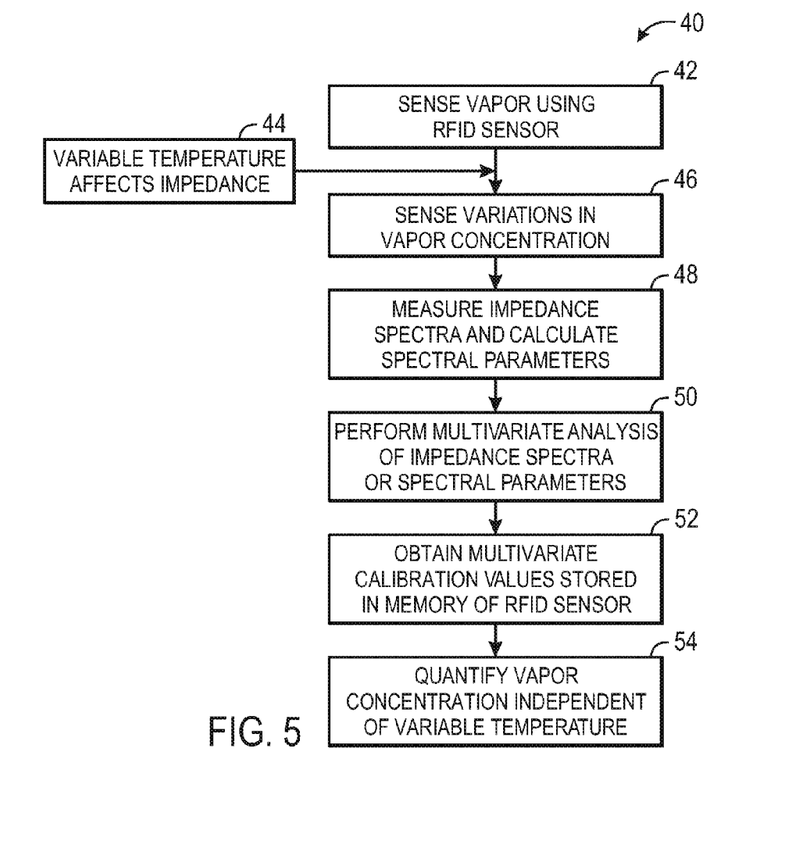
FIG. 5 is a flow chart that shows a process for analyzing a vapor in the presence of variable temperature, in accordance with embodiments of the invention.

FIG. 5 is a flow chart 40 that shows an exemplary process for analyzing a vapor in the presence of variable temperature using the RFID sensor 12 or 21, in which the temperature-dependent response coefficients of impedance of the sensing material 14 and the other components of the RFID sensor 12 or 21 are not the same. In the following steps, multivariate analysis of the measured impedance of the RFID sensor 12 or 21 is used to provide a temperature-independent vapor response. In a first step 42, the RFID sensor 12 or 21 performs sensing of a vapor via monitoring of the changes in the properties of the sensing material 14 as probed by the electromagnetic field generated in the antenna 18 as described in detail above. In a second step 44, temperature fluctuations occur that affect the impedance of the RFID antenna circuit and sensing material 14. However, the impedances of the RFID antenna circuit and sensing material 14 are not equally affected because of the differences in the temperature-dependent response coefficients of impedance of the RFID antenna circuit and sensing material 14. In addition, the differences in the temperature-dependent response coefficients of impedance of the RFID antenna circuit and sensing material 14 affect the measured impedance spectra of the resonant antenna. In a third step 46, the RFID sensor 12 or 21 senses variations in the concentration of the vapor to be quantified. Temperature fluctuations may continue to occur in the third step 46. In a fourth step 48, the RFID sensor 12 or 21 measures the impedance spectra of the resonant antenna. Several spectral parameters may be calculated from the measured real and imaginary portions of the impedance spectra as described in detail above. In a fifth step 50, multivariate analysis of the full impedance spectra or the calculated spectral parameters is performed, as described in detail below.

In a sixth step 52, appropriate multivariate calibration values, or calibration coefficients, stored in the memory chip 16 of the RFID sensor 12 or 21 are obtained. The calibration coefficients are determined during experimental testing of the RFID sensor 12 or 21. For example, the RFID sensor 12 or 21 is used to sense varying vapor concentrations at several temperatures. PCA, or any other multivariate analysis method or combination of methods, may then be used to produce response curves for each of the measured temperatures. Best-fit curves that best correspond to each of the response curves are determined and functions, such as polynomial functions, are determined to represent the best-fit curves mathematically. Each function includes several numerical coefficients that characterize the function. These coefficients are then used as the calibration coefficients, which may be stored in the memory chip 16 as a look-up table, for example. During operation, the concentration and/or temperature of the vapor sensed by the RFID sensor 12 or 21 may not correspond to one of the experimental concentrations or temperatures. However, using the experimentally determined calibration coefficients in the look-up table, an interpolated function (i.e. response curve) may be generated that best represents the predicted behavior of the vapor at the sensed concentration and temperature.

In a seventh step 54, the RFID sensor 12 or 21 quantifies the concentration of the vapor independent of the variable temperature based on the multivariate analysis performed in the fifth step 50 and the response curve determined in the sixth step 52. Specifically, the results of the multivariate analysis of the fifth step 50 are substituted into the interpolated function determined in the sixth step 52 to calculate the vapor concentration. The calculated vapor concentration is accurate because the effect of the variable temperature on the RFID sensor 12 or 21 has been accounted for in the preceding steps of the flow chart 40. As illustrated in the flow chart 40, there is no need for a separate temperature sensor because the individual RFID sensor 12 or 21 is capable of providing the temperature-independent vapor response based on the multivariate analysis of the measured impedance values. Thus, the RFID sensor 12 may be smaller, less expensive, less complicated, and/or more reliable than other sensor systems that use a separate temperature sensor.

Diverse sensing materials may be advantageously utilized on the sensing region of the LCR resonant sensor because analyte-induced changes in the sensing material film affect the impedance of the antenna LCR circuit through the changes in material resistance and capacitance, contact resistance and capacitance between the transducer and sensing material, and resistance and capacitance between the transducer substrate and sensing material. Such changes provide diversity in response of an individual RFID sensor and provide the opportunity to replace a whole array of conventional sensors with a single LCR or RFID sensor.

Sensing films for the disclosed LCR and RFID sensors may include a variety of materials, as long as the environmental changes are detectable by changes in resonant LCR circuit parameters. In addition, a temperature-dependent response coefficient of a property of the sensing films is different from that of the LCR circuit, as described in detail above. Non-limiting examples of possible sensing film materials are a hydrogel such as poly(2-hydroxyethyl methacrylate), a sulfonated polymer such as Nafion, an adhesive polymer such as silicone adhesive, an inorganic film such as sol-gel film, a biological-containing film such as DNA, antibody, peptide or other biomolecules deposited as a film, a biological-containing film such as DNA, antibody, enzyme, peptide, polysaccharide, protein, aptamer, or other biomolecules or viruses, spores, cells, deposited as a part of a inorganic or polymeric film, a composite film, a nanocomposite film, functionalized carbon nanotube film, or film made of surface functionalized gold nanoparticles, electrospun polymeric, inorganic, and composite nanofibers, and nanoparticles that have one dielectric property and incorporated in a matrix that have another dielectric property.

Sensing materials can be selected to have different dielectric constants ranging from about 2 to about 40. Non-limiting examples include polyisobutylene (PIB, $\in'_r=2.1$), ethyl cellulose (EC, $\in'_r=3.4$), polyepichlorihydrin (PECH, $\in'_r=7.4$), cyanopropyl methyl phenylmethyl silicone (OV-225, $\in'_r=11$), dicyanoallyl silicone (OV-275, $\in'_r=33$). The use of these materials provides the ability to tailor the relative direction of sensing response upon exposure to vapors of different dielectric constant. The different partition coefficients of vapors into these or other sensing materials further modulate the diversity and relative direction of the response.

"Composites" are materials made from two or more constituent materials with significantly different physical or chemical properties, which remain separate and distinct on a macroscopic level within the finished structure. For example, the two or more constituent materials may have different temperature-dependent response coefficients for a property, such as impedance. Non-limiting examples of composites include carbon black composites with poly(4-vinylphenol), poly(styrene-co-allyl alcohol), poly(vinyl chloride-covinyl acetate), and other materials. "Nanocomposites" are materials made from two or more constituent materials with significantly different physical or chemical properties, which remain separate and distinct on a nanoscale level within the finished structure. Non-limiting examples of nanocomposites include: carbon nanotube nanocomposites with polymers (such as poly(N-vinylpyrrolidone), polycarbonate, polystyrene, etc.); semiconducting nanocrystal quantum dot nanocomposites with polymers, metal oxide nanowires, and carbon nanotubes; metal nanoparticles or nanoclusters functionalized with carbon nanotubes.

Sensing materials exhibit analyte responses, which can be described by one or more of three response mechanisms of LCR or RFID sensors, such as resistance changes, dielectric constant changes, and swelling changes. A composite sensing material can be constructed which incorporates multiple different individual sensing materials, which each respond to analytes by predominantly different response mechanisms. Such composite sensing materials produce an enhanced diversity in the multivariate response. Such composite sensing materials may be homogeneously or inhomogeneously mixed or locally patterned over specific portions of the LCR resonator.

For example, a wide range of metal oxide semiconductor materials (e.g. $ZnO$, $TiO_2$, $SrTiO_3$, $LaFeO_3$, etc) exhibit changes in resistance upon exposure to analyte gases, but some mixed metal oxides (e.g. $CuO$—$BaTiO_3$, $ZnO$—$WO_3$) change their permittivity/capacitance upon exposure to analyte vapors. By combining these materials either as mixtures, or by spatially separated deposition onto the same sensor, their separate contributions to the local environment surrounding the sensor are used to enhance the diversity of response mechanisms for a single analyte, thus enhancing selectivity.

As a further example, ligand-coated conducting (e.g. metal) nanoparticles are used as vapor sensing materials because of their strong changes in resistance due to localized swelling induced by analyte adsorption into the ligand shell and the subsequent change in tunneling efficiency between neighboring conducting nanoparticles and dielectric constant changes of the environment between these conducting nanoparticles. In combination with a dielectric polymer (non-limiting examples include silicones, poly(etherurethane), polyisobutylene siloxane fluoroalcohol, etc.), conjugated polymer (polyaniline, polythiophene, poly(vinyl ferrocene), poly(fluorene)-diphenylpropane), poly(3,4-ethylenedioxythiophene)polypyrrole, bilypyrrole) or any other material (non-limiting examples include porphyrins, metalloporphyrins, metallophthalocyanines, carbon nanotubes, semiconducting nanocrystals, metal oxide nanowires) that responds to analyte adsorption with more pronounced changes in capacitance or resistance, a sensor with a wider range of analyte responses is developed.

Further, in order to avoid potentially deleterious effects of disparate materials on each other in a composite sensing material (e.g. high dielectric constant medium suppressing conduction in a conductive filler material), this material components are chosen to locally phase separate due to hydrophilic/hydrophobic interactions or mutual immiscibility, allowing the different mechanisms active in each component to be sensed by the sensor. In another embodiment, a composite sensing material can be formed as sectors of individual materials deposited adjacent to each other onto a single sensor. In another embodiment, a composite sensing material can be formed as layers of individual materials deposited on top of each other onto a single sensor.

In certain embodiments, sensing materials may be porphyrins, metalloporphyrins, metallophthalocyanines, and related macrocycles. In these materials, gas sensing is accomplished either by $\pi$-stacking of the gas into organized layers of the flat macrocycles or by gas coordination to the metal center without the cavity inclusion. Metalloporphyrins provide several mechanisms of gas response including hydrogen bonding, polarization, polarity interactions, metal center coordination interactions and molecular arrangements. Molecules of porphyrins, metalloporphyrins, metallophthalocyanines, and related macrocycles can be also assembled into nanostructures.

Further types of materials include aligned nanostructures where alignment is performed by various known methods (dielectrophoretic alignment, alignment during material polymerization, alignment due to spatial confinement, alignment during slow solvent evaporation, and others), self-assembled structures such as colloidal crystal structures of the same size of particles, multilayers of colloidal crystal films where different layers have different size of assembled particles, nanoparticle assemblies where the particles have core-shell structure with the particle core of one dielectric property and particle shell of another dielectric property, bio-inspired materials, zero-dimensional nanomaterials, one-dimensional nanomaterials, two-dimensional nanomaterials, and three-dimensional nanomaterials.

Self-assembled structures include colloidal crystal structures of the same size of particles, multilayers of colloidal crystal films where different layers have different sizes of assembled particles, nanoparticle assemblies where the particles have core-shell structure with the particle core of one dielectric property and particle shell of another dielectric property. Non-limiting examples of materials of self-assembled colloidal crystal structures include polystyrene, polymethylmethacrylate, polyvinyltoluene, styrene/butadiene copolymers, styrene/vinyltoluene copolymers, and silica. The typical diameters of these colloidal particles depend on the type of material and may range from 50 nanometers to 25 micrometers. Non-limiting examples of colloidal crystal structures with multiple layers include at least one layer of particles of one size assembled as a colloidal array onto the sensor substrate and at least one layer of particles of another size assembled as a colloidal array on top of the previous layer. Non-limiting examples of bio-inspired materials include super hydrophobic or superhydrophilic coatings.

Non-limiting examples of zero-dimensional nanomaterials include metal nanoparticles, dielectric nanoparticles, core-shell nanoparticles, and semiconducting nanocrystals. Non-limiting examples of one-dimensional nanomaterials include nanotubes, nanowires, nanorods, and nanofibers. Non-limiting examples of two-dimensional nanomaterials include graphene. Non-limiting examples of three-dimensional nanomaterials include self-assembled films of several layers of colloidal spheres.

Non-limiting examples of nanoparticles that have core-shell structure with the particle core of one dielectric property and particle shell of another dielectric property include: metal (gold, silver, their alloy, etc.) core nanoparticles and organic shell layers (dodecanethiol, decanethiol, 1-butanethiol, 2-ethylhexanethiol, hexanethiol, tert-dodecanethiol, 4-methoxy-toluenethiol, 2-mercaptobenzoxazole, 11-mercapto-1-undecanol, 6-hydroxyhexanethiol); polymeric core (polystyrene, polymethylmethacrylate) and inorganic shell (silica); isolating core (polystyrene, polymethylmethacrylate, silica) and semiconducting shell (carbon nanotubes, $TiO2$, $ZnO$, SnO2, WO3), and carbon nanotube core that is decorated with metal nanoparticles. The nanoparticles of metal (gold, silver, their alloy, etc.) core nanoparticles and organic shell layers can be further modified with organic and polymeric molecules. Non-limiting example of organic molecules include porphyrins, metalloporphyrins, metallophthalocyanines, and macrocycles, cavitands, surpamolecular compounds. Non-limiting example of polymeric molecules include polymeric molecules with different dielectric constants ranging from 2 to 40. Non-limiting examples include polyisobutylene (PIB, $\in'_r=2.1$), ethyl cellulose (EC, $\in'_r=3.4$), polyepichlorihydrin (PECH, $\in'_r=7.4$), cyanopropyl methyl phenylmethyl silicone (OV-225, $\in'_r=11$), dicyanoallyl silicone (OV-275, $\in'_r=33$). A non-limiting example of fabrication of these sensing materials involves (1) preparation of metal core nanoparticles with an organic shell in a solvent, (2) mixing this composition with another composition of polymeric or organic molecules in a solvent, and (3) making a sensing film on an LCR or RFID transducer from this combined mixture. The use of these materials in combination with metal core nanoparticles provides the ability to tailor the relative direction of sensing response upon exposure to vapors of different dielectric constant. The different partition coefficients of vapors into these or other sensing materials further modulate the diversity and relative direction of the response.

Other sensing materials include semiconducting metal oxides, zeolites, cavitands, ionic liquids, liquid crystals, crown ethers, enzymes, polysilsesquioxanes, metal-organic frameworks (MOFs).

Other sensing materials include synthetic dielectric and conducting polymers with different polymer side group functionalities, and different polymer formulations; biomolecules for gas-phase sensing; cavitands with dominating intracavity complexation and a totally suppressed non specific extracavity adsorption of vapors provided by cavitand deposition; porphyrins and related molecules as individual molecules and as assembled into polymers and nanostructures.

To further improve temperature-corrected response, overcoating of sensing films with auxiliary membrane filter films may be performed. Non-limiting examples of these filter films include zeolite, metal-organic framework, and cavitand filters.

These diverse sensing materials shown as non-limiting examples are provided on the sensing region of the LCR or RFID resonant sensor because analyte-induced changes in the sensing material film affect the impedance of the antenna LCR circuit through the changes in material resistance and capacitance, contact resistance and capacitance between the transducer and sensing material, resistance and capacitance between the transducer substrate and sensing material. Such changes provide diversity in response of an individual RFID sensor and provide the opportunity to replace a whole array of conventional sensors with a single LCR or RFID sensor, as illustrated further below, with regard to EXPERIMENTAL DATA.

EXPERIMENTAL DATA

Resonant antenna structures, such as those described above, were used for demonstration of the disclosed techniques. Various sensing materials were applied onto the resonant antennas by conventional draw-coating, drop coating, and spraying processes. Measurements of the impedance of the RFID sensors were performed for example with a network analyzer (Model E5062A, Agilent Technologies, Inc., Santa Clara, Calif.) under computer control using LabVIEW. The network analyzer was used to scan the frequencies over the range of interest (i.e., the resonant frequency range of the LCR circuit) and to collect the impedance response from the RFID sensors. Temperature changes were produced by placing the RFID sensor into an environmental chamber and controlling the temperature with approximately 0.1 degree Celsius precision and accuracy.

For gas sensing, different concentrations of vapors were generated using an in-house built computer-controlled vapor-generation system. Collected impedance data was analyzed using Excel (MicroSoft Inc. Seattle, Wash.) or KaleidaGraph (Synergy Software, Reading, Pa.) and PLS_Toolbox (Eigenvector Research, Inc., Manson, Wash.) operated with Matlab (The Mathworks Inc., Natick, Mass.).

EXAMPLE

Figure 6:
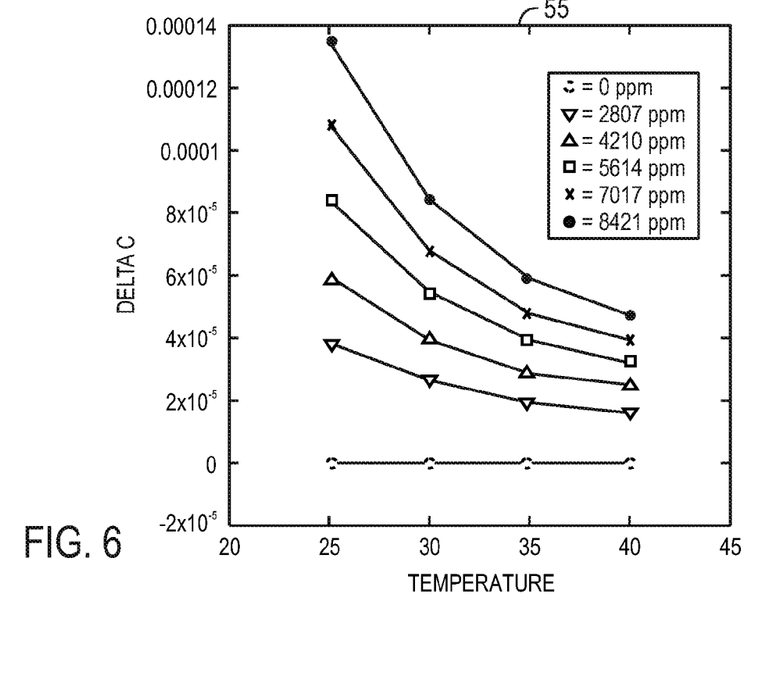
FIGS. 6-11 illustrate test data demonstrating a single sensor capable of discriminating between humidity levels independent of temperature, in accordance with embodiments of the invention.
Figure 7:
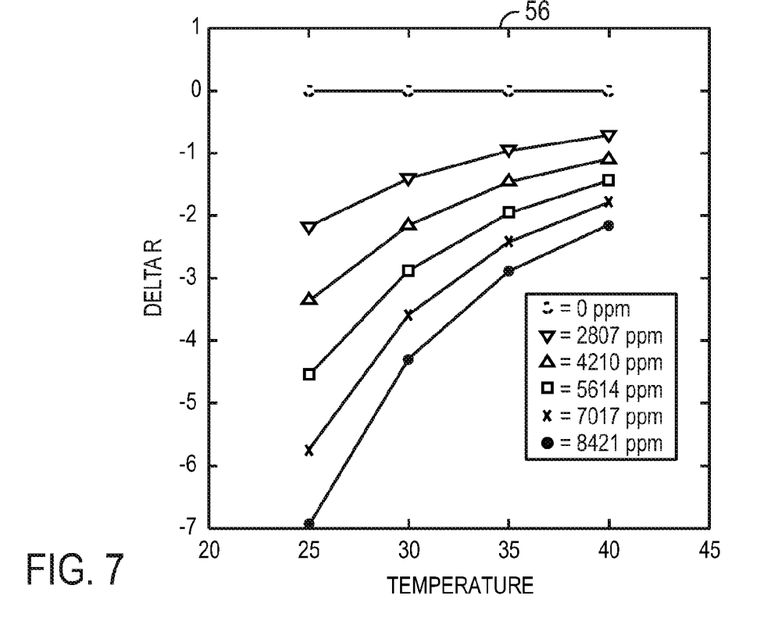
Figure 8:
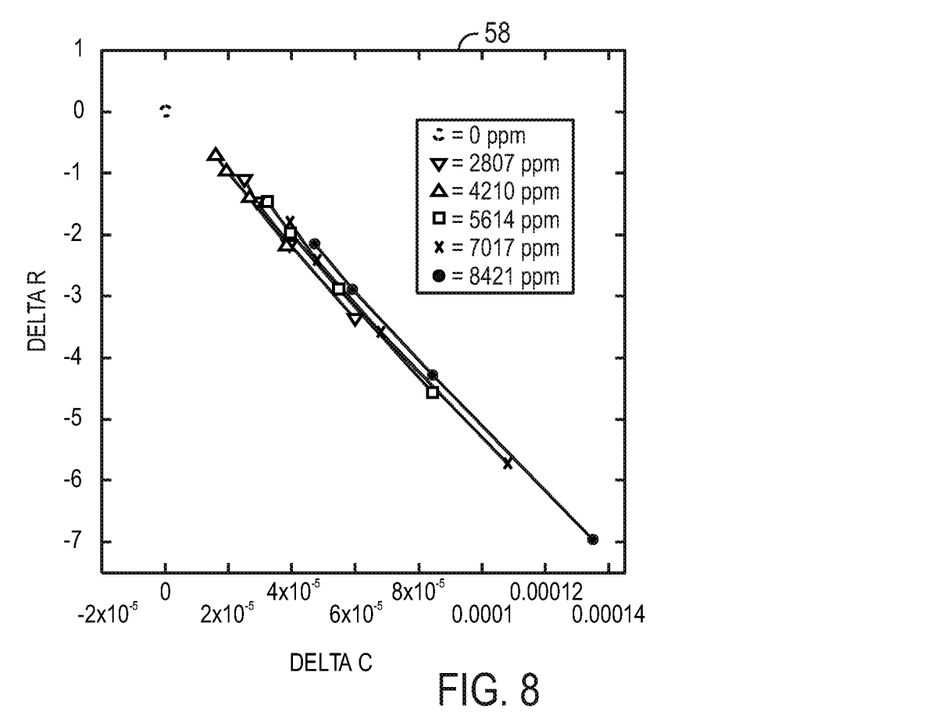
Figure 9:
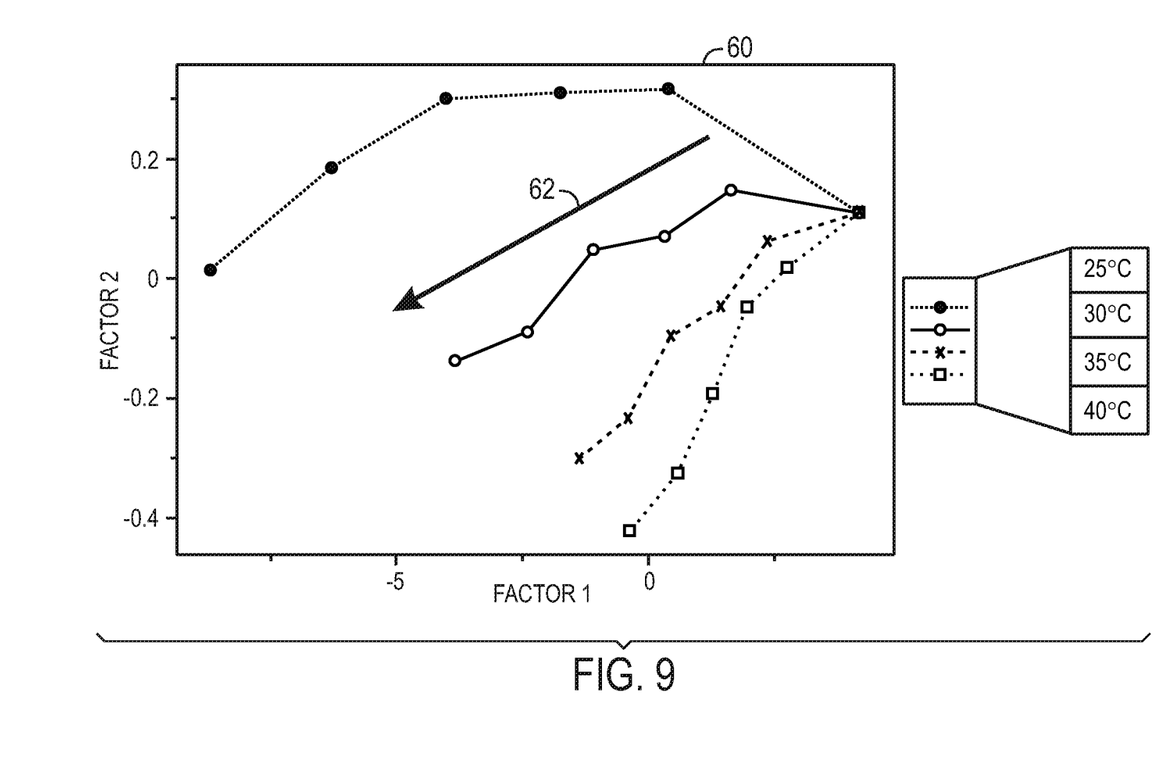
Figure 10:
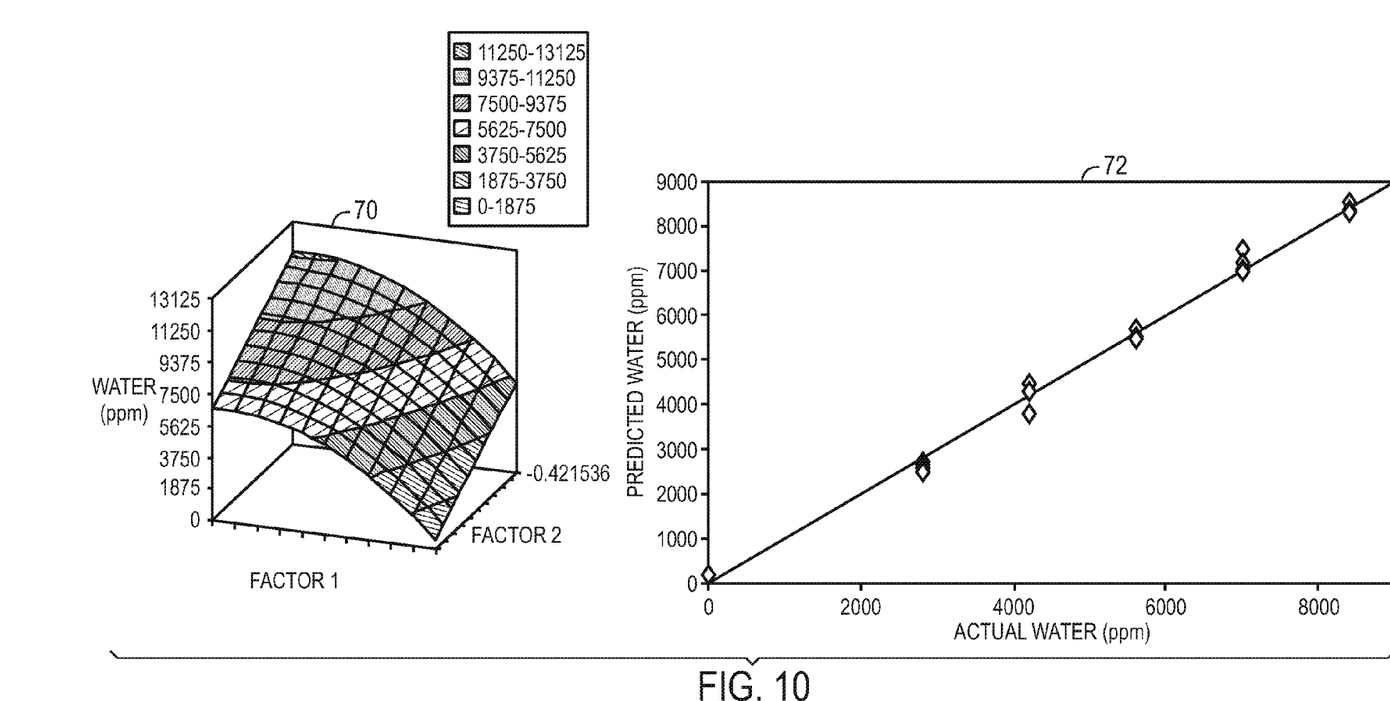

Accurate Detection of Humidity Levels at Different Temperatures with a Single Sensor As illustrated in FIGS. 6-11, test results were obtained to demonstrate the accurate detection of water vapor at several different temperatures, using a single sensor, such as the sensor 12 described above. Such test results may be used to generate the calibration coefficients discussed above with respect to FIG. 5. As illustrated in FIGS. 6, 7, and 9, the sensor was exposed to varying concentrations of water vapor at the following temperatures: 25 degrees Celsius, 30 degrees Celsius, 35 degrees Celsius, and 40 degrees Celsius. Tested concentrations of the water vapor were approximately 0 ppm, 2807 ppm, 4210 ppm, 5614 ppm, 7017 ppm, and 8421 ppm.

The sensing material used to coat the RFID tag was carefully chosen and provided the ability to accurately detect the concentrations of the water vapor at the four temperatures. In the present experiment, the chosen sensing material was poly (etherurethane) (PEUT) dissolved in a nonpolar solvent such as dichloromethane. During the experiment, the RFID sensor was incrementally exposed to the various water vapor concentrations at each of the four temperatures. Specifically, measurements were performed by positioning the sensor in an environmental chamber with computer controlled temperature programming. Generation of different concentrations of water vapor was performed using a vapor-generation system with computer controlled vapor concentration programming. The test was conducted in steps, where the concentration of the water vapor was increased with each step. By monitoring changes in certain properties and examining various responses over the four temperatures and at increasing concentration levels, the data demonstrated the ability to accurately quantify water vapor concentration independent of temperature in the above-described experiment.

FIGS. 6 and 7 illustrate examples of temperature effects on the individual responses of the RFID sensor when the RFID sensor was employed for measurements of a vapor (i.e., water vapor in this example). The graphs 55 and 56 show a significant temperature dependence of capacitance response C and resistance response R of the sensor coated with the film upon sensor exposure to water vapor concentrations of approximately 0, 2807, 4210, 5614, 7017, and 8421 ppm. In other words, the capacitance and resistance response change with respect to temperature. In FIG. 8, the capacitance response C is plotted against the resistance response R of the sensor coated with the film for different temperatures of approximately 25, 30, 35, and 40 degrees Celsius and upon exposure to water vapor concentrations of approximately 0, 2807, 4210, 5614, 7017, and 8421 ppm. Each line in FIG. 8 corresponds to the sensor response at a particular concentration of water vapor at different temperatures. For example, the line with solid circles corresponds to the sensor response to 8421 ppm of water vapor at four temperatures. The top left portion of the line corresponds to the response at 40 degrees Celsius, while the bottom right portion of the line corresponds to the response at 25 degrees Celsius. FIG. 8 illustrates that temperature significantly affects the relationship between the capacitance and resistance responses. Thus, it is difficult to distinguish between temperature and water vapor concentration effects based on FIG. 8. However, by applying multivariate analysis of sensor response, as described below, significant improvements in discriminating between temperature and vapor concentration effects is obtained.

One convenient way of analyzing various responses of the sensor is to use principal components analysis (PCA) to produce a multivariate signature. As will be appreciated, PCA analysis is a mathematical process, known to those skilled in the art, that is used to reduce multidimensional data sets to lower dimensions for analysis. For instance, the various responses for each vapor at a given concentration may be reduced to a single data point, and from this, a single response for each vapor, which may be represented as a vector, may be discerned, as illustrated in FIG. 9. FIG. 9 represents a PCA plot 60 of the various responses of the six concentrations of water vapor at the four temperatures described above. The water vapor concentrations increase in the direction of arrow 62. In other words, the results at the highest concentration of the water vapor, namely 8421 ppm, appear near the left side of the plot 60 and the results at the lowest concentration of 0 ppm appear near the right side of the plot 60, with the results at 0 ppm overlapping into a single data point for the four temperatures. As will be appreciated, FACTOR 1 represents the response with the most variation, while FACTOR 2 represents the response with the next most variation. Compared to FIG. 8, the lines representing different vapor concentrations in FIG. 9 are spread further apart, indicating the improvements in discriminating between temperature and vapor concentration effects made possible by multivariate analysis. As shown in FIG. 9, although the water vapor concentrations display a greater change with respect to FACTOR 1 at 25 degrees Celsius compared to at 40 degrees Celsius, the results at the four temperatures are clearly distinguishable from one another. Thus, sensors according to various embodiments are capable of correcting for these temperature effects to provide accurate water vapor concentration information. Specifically, best-fit curves and corresponding functions may be developed for each of the four temperatures. The coefficients of these functions may then be used as the calibration coefficients described in detail above. Accordingly, the instant test data provides support for a sensor capable of discerning between water vapor concentrations independent of temperature.

Using the functions and calibration coefficients based on data collected at experimental temperatures, the effect of temperature on sensor measurements at other temperatures may be extrapolated or interpolated. For instance, one may be able to extrapolate water vapor concentrations between 25 degrees Celsius and 30 degrees Celsius. Such additional extrapolated data may also be used to selectively detect water vapor concentrations at other temperatures. Further, by varying the selected sensing material, selective detection of vapors other than water, at temperatures and concentrations other than those described above, has been demonstrated utilizing a single RFID sensor.

Other plots may be generated to further show how experimental data collected for a single RFID sensor is used to quantify water vapor concentrations independent of temperature. For example, the data from FIG. 9 was used to generate the multivariate response plot 70 of FACTOR 1 and FACTOR 2 of a developed quadratic model compared to water vapor concentration illustrated on the left of FIG. 10. In other words, a quadratic model was developed to represent the results of the PCA plot 60 shown in FIG. 9. Predicted values of water vapor concentration at the various conditions described in detail above were calculated using the quadratic model and compared with the actual measured values in plot 72 of FIG. 10. As illustrated in plot 72 of FIG. 10, the points lie close to a line corresponding to a slope of one. For example, the standard error of the quadratic model is approximately 212 ppm of water vapor (i.e., 0.7 percent relative humidity). Thus, the predicted values are closely correlated to the actual values, demonstrating the predictability of the exemplary sensor and method.

Figure 11:
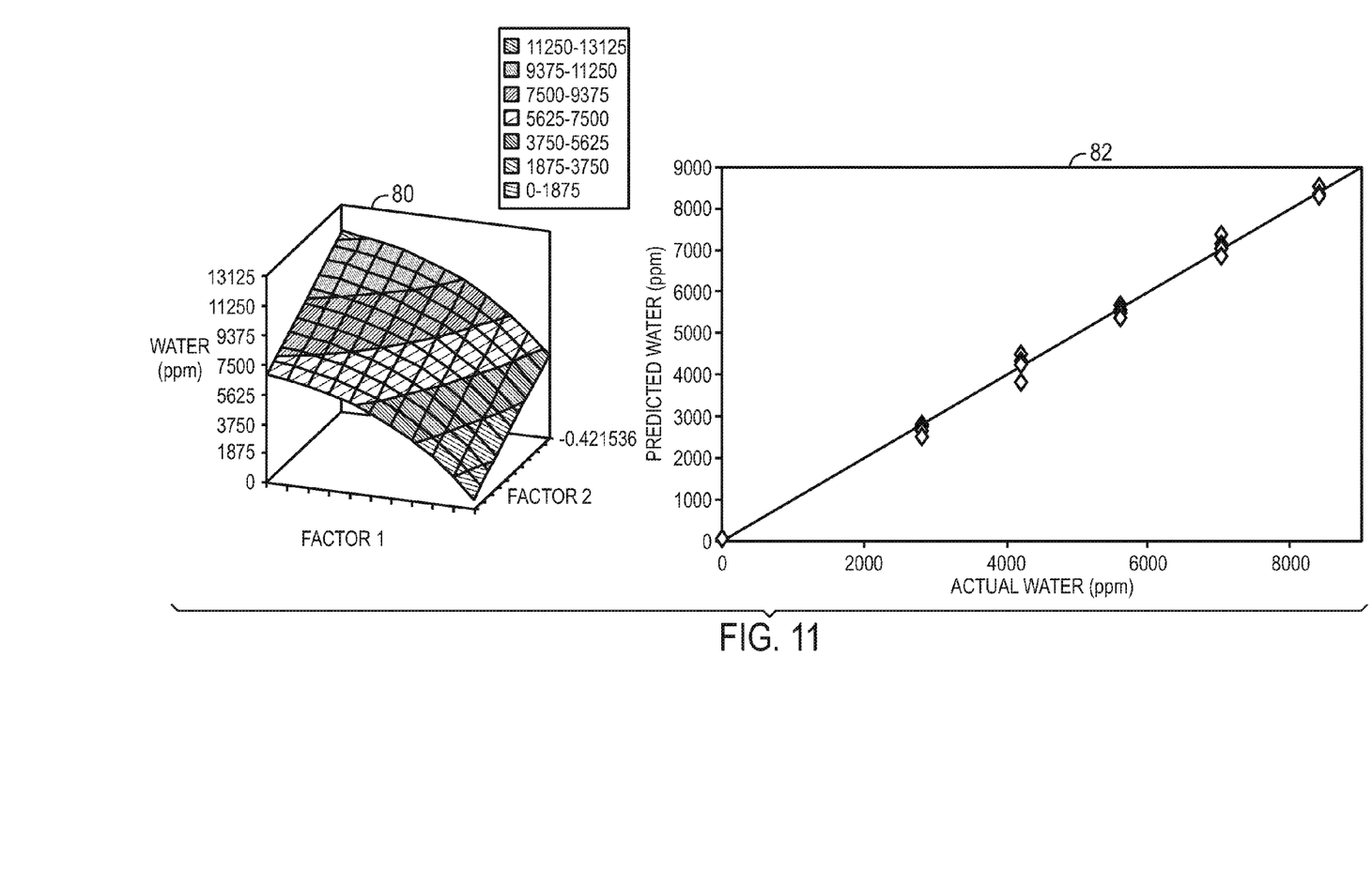

Similarly, data from FIG. 9 was used to generate the multivariate response plot 80 of FACTOR 1 and FACTOR 2 of a developed cubic model compared to water vapor concentration illustrated on the left of FIG. 11. In other words, a cubic model was developed to represent the results of the PCA plot 60 shown in FIG. 9. Predicted values of water vapor concentration at the various conditions described in detail above were calculated using the cubic model and compared with the actual measured values in plot 82 of FIG. 11. As illustrated in plot 82 of FIG. 11, the points lie close to a line corresponding to a slope of one. For example, the standard error of the quadratic model is approximately 188 ppm of water vapor (i.e., 0.63 percent relative humidity). Thus, as with the quadratic model of FIG. 10, the predicted values are closely correlated to the actual values, again demonstrating the predictability of the exemplary sensor and method. In further embodiments, other polynomial models, besides quadratic and cubic models, may also be used.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of detecting chemical or biological species in a fluid, comprising:
    measuring, with a network analyzer, a real part and an imaginary part of an impedance spectrum of a single resonant sensor antenna coated with a sensing material, wherein temperature-dependent response coefficients of a property of the single resonant sensor antenna and the sensing material are different from one another;
    calculating, with a network analyzer, at least six spectral parameters of the single resonant sensor antenna coated with the sensing material at a plurality of temperatures;
    reducing, with a first processor configured to perform canonical correlation analysis, regression analysis, non-linear regression analysis, principal components analysis, discriminate function analysis, multidimensional scaling, linear discriminate analysis, logistic regression, or neural network analysis, the impedance spectrum to a single data point using multivariate analysis to selectively identify an analyte; and
    determining, with the first processor or a second processor, one or more environmental parameters from the impedance spectrum using stored calibration coefficients, wherein the determination of the one or more environmental parameters is substantially independent of temperature.

2. The method, as set forth in claim 1, wherein the stored calibration coefficients are based on the effects on the impedance spectrum of the different temperature-dependent response coefficients of the property of the single resonant sensor antenna and the sensing material.

3. The method, as set forth in claim 1, wherein measuring the impedance spectrum and calculating at least six spectral parameters comprises measuring over a resonant frequency range of the resonant sensor antenna.

4. The method, as set forth in claim 1, wherein calculating at least six spectral parameters comprises calculating a frequency position of the real part of the impedance spectrum, and a magnitude of the real part of the impedance spectrum.

5. The method, as set forth in claim 1, wherein calculating at least six spectral parameters comprises calculating a resonant frequency of the imaginary part of the impedance spectrum, and an anti-resonant frequency of the imaginary part of the impedance spectrum.

6. The method, as set forth in claim 1, wherein reducing the impedance spectrum to a single data point comprises calculating a multivariate signature.

7. The method, as set forth in claim 1, comprising operating an integrated circuit chip at a plurality of power levels such that a resonant inductor-capacitor-resistor (LCR) circuit is operated at a plurality of conditions.

8. The method, as set forth in claim 7, wherein the operation of the LCR circuit at the plurality of conditions improves the temperature-independent determination of the one or more environmental parameters.

9. The method, as set forth in claim 1, comprising:
acquiring an impedance spectrum over a resonant frequency range of a resonant sensor circuit having the single resonant sensor antenna; and
calculating a multivariate signature from the acquired impedance spectrum.

10. A method of manufacturing a sensor, comprising:
assembling, with at least one inductor, at least one capacitor, and at least one resistor, a transducer comprising a single resonant inductor-capacitor-resistor (LCR) circuit, wherein the transducer comprises at least three temperature-dependent response coefficients of inductance L, capacitance C, and resistance R properties of the single LCR circuit, wherein the at least three temperature-dependent response coefficients of the properties of the single LCR circuit are at least approximately 5 percent different from one another;
selecting a sensing material, from at least one of a hydrogel, a sulfonated polymer, an adhesive polymer, an inorganic film, a biological-containing film, a composite film, a nanocomposite film, functionlized carbon nanotube film, film made of surface functionalized gold nanoparticles, electrospun polymeric, inorganic, and composite nanofibers, and/or nanoparticles that have one dielectric property and incorporated in a matrix that has another dielectric property, wherein the sensing material comprises at least two temperature-dependent response coefficients of dielectric constant and resistance properties of the sensing material, wherein the at least two temperature-dependent response coefficients of the properties of the sensing material are at least approximately 5 percent different from the at least three temperature-dependent response coefficients of the properties of the single LCR circuit;
disposing, by draw-coating, drop coating, or spraying processes, the sensing material over a sensing region, wherein the sensing region comprises at least a portion of the single LCR circuit.

11. The method, as set forth in claim 10, wherein the difference in the first and second temperature-dependent response coefficients of the property enables the sensor to provide substantially temperature-independent sensing.

12. The method, as set forth in claim 10, wherein the sensor is configured to acquire an impedance over a resonant frequency range of the transducer at a plurality of temperatures and calculate a multivariate signature from the acquired impedance spectrum at the plurality of temperatures using stored calibration coefficients based on the difference in the first and second temperature-dependent response coefficients of the property.

13. A method of detecting analytes in a fluid, comprising:
acquiring, with a network analyzer, an impedance spectrum over a resonant frequency range of a single resonant sensor circuit having a sensing material, wherein temperature-dependent response coefficients of a property of the single resonant sensor circuit and the sensing material are different from one another; and
calculating, using a processor configured to perform principal components analysis, a multivariate signature from the acquired impedance spectrum.

14. The method, as set forth in claim 13, wherein calculating a multivariate signature from the acquired impedance spectrum is performed using the real part of the impedance spectrum.

15. The method, as set forth in claim 13, wherein the resonant frequency range is within a range of 0.1 Hz-1000 THz.

16. The method, as set forth in claim 13, wherein acquiring the impedance spectrum is performed in a fluid having greater than 50% humidity.

17. The method, as set forth in claim 13, wherein the multivariate signature is calculated using principal components analysis, canonical correlation analysis, regression analysis, nonlinear regression analysis, discriminate function analysis, multidimensional scaling, linear discriminate analysis, logistic regression, or neural network analysis.

18. The method, as set forth in claim 13, wherein acquiring the impedance spectrum comprises detecting dielectric, dimensional, resistance, charge transfer or other changes of material properties by monitoring changes in properties of the resonant circuit.

19. The method, as set forth in claim 13, wherein the resonant circuit comprises an inductor-capacitor-resistor (LCR) circuit.

20. The method, as set forth in claim 13, comprising:
measuring a real part and an imaginary part of the impedance spectrum of a resonant sensor antenna of the single resonant sensor circuit, wherein the resonant sensor antenna is coated with a sensing material;
calculating at least six spectral parameters of the single resonant sensor circuit coated with the sensing material;
reducing the impedance spectrum to a single data point using multivariate analysis to selectively identify the analyte; and
determining one or more environmental parameters from the impedance spectrum.

* * * * *